United States Patent [19]

Becherer et al.

[11] Patent Number: 4,517,370
[45] Date of Patent: May 14, 1985

[54] PROCESS FOR PREPARING 2-CHLOROBENZOXAZOLES

[75] Inventors: Johannes Becherer, Maintal; Klaus Kühlein, Kelkheim; Ulrich Kussmaul, Niederdorfelden, all of Fed. Rep. of Germany

[73] Assignee: Cassella Aktiengesellschaft, Frankfurt am Main, Fed. Rep. of Germany

[21] Appl. No.: 467,742

[22] Filed: Feb. 18, 1983

[30] Foreign Application Priority Data

Feb. 27, 1982 [DE] Fed. Rep. of Germany ....... 3207153

[51] Int. Cl.³ .......................................... C07D 263/54
[52] U.S. Cl. ................................................. 548/217
[58] Field of Search ................................ 548/217, 221

[56] References Cited

U.S. PATENT DOCUMENTS 3,284,294  11/1966  Sasse et al. ......................... 548/217

FOREIGN PATENT DOCUMENTS 1210617  8/1966  Fed. Rep. of Germany ....... 548/217

OTHER PUBLICATIONS

J. pr. Chemie, 42, 454, (1980).
Boll. Sci. Fac. Chem. Ind. Bologna 23, (2–3), 89 to 98, (1965).

Primary Examiner—Nicholas S. Rizzo
Assistant Examiner—S. A. Gibson
Attorney, Agent, or Firm—Connolly and Hutz

[57] ABSTRACT

In the process for preparing 2-chlorobenzoxazoles of the formula

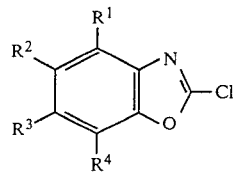

wherein each of $R^1$, $R^2$, $R^3$ and $R^4$ is independently of one another, H, chloro or alkyl having 1 to 4 carbon atoms, which comprises reacting chlorine with 2-mercaptobenzoxazoles of the formula

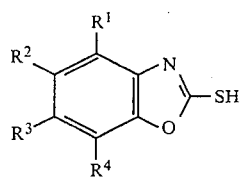

wherein the improvement comprises providing a melt of previously prepared 2-chloro-benzoxazole, adding the 2-mercaptobenzoxazole reactant to the 2-chlorobenzoxazole melt and simultaneously or subsequently passing chlorine into the melt, with the proviso that substituents $R^1$ to $R^4$ are identical in both the 2-chlorobenzoxazole melt and the 2-mercaptobenzoxazole reactant.

11 Claims, No Drawings

PROCESS FOR PREPARING 2-CHLOROBENZOXAZOLES

The invention relates to a process for preparing 2-chlorobenzoxazoles of the formula I

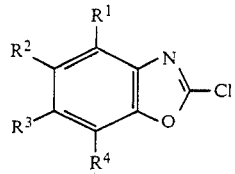

in which $R^1$, $R^2$, $R^3$ and $R^4$ independently of one another denote H, Cl or alkyl having 1 to 4 C atoms by reacting 2-mercaptobenzoxazoles of the formula II

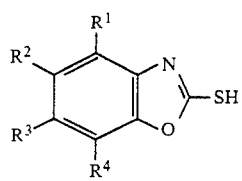

with chlorine.

The preparation of 2-chlorobenzoxazole from 2-mercaptobenzoxazole and chlorine or chlorine-donating agents is known, cf. J.pr.Chemie 42, 454 (1890); Am. Chemical Journal 21, 123 (1899); Boll. Sci. Fac. Chim. Ind. Bologna 23 (2-3) 89-98 (1965); German Pat. No. 1,164,413; and German Pat. No. 1,210,617. All known processes have disadvantages. In the case of processes where a large amount of an inert solvent or suspending medium is used, these disadvantages reside in particular in the poor space-time yield and the associated high investment costs, in the large amount of energy required for distilling off the solvent and in the difficult separation of the reaction mixture into its components. Thus, for example, it is difficult to separate the sulphur chlorides which are formed in the chlorination with chlorine from low-boiling solvents, but, on the other hand, when higher-boiling solvents are used it is involved to separate solvent and product.

Only two processes have been described which do not use solvents. In one of the processes (J.pr.Chemie 42, 454 (1890)), partial carbonisation always occurs and results in a considerable reduction in yield. In the other process (Boll. Sci. Fac. Chim. Ind. Bologna 23 (2-3) 89-98 (1965)), no yield is indicated but the working-up is very involved. If the batch is worked up by distillation, the yield is only 85% of theory. There is moreover a large distillation residue, the elimination of which presents problems when the preparation is carried out on a relatively large scale.

It has now been found, surprisingly, that it is possible to prepare 2-chlorobenzoxazoles of the formula I in high yield and purity by reacting 2-mercaptobenzoxazoles of the formula II with chlorine without using an additional solvent or catalyst if 2-mercaptobenzoxazole of the formula II is added to a melted 2-chlorobenzoxazole of the formula I where the two compounds are identically substituted in the radicals $R^1$ to $R^4$, and chlorine is passed in afterwards or at the same time.

In carrying out the process according to the invention, a small amount of a melted 2-chlorobenzoxazole of the formula I is initially introduced, 2-mercaptobenzoxazole of the formula II is added with stirring, and chlorine is passed in. Relative to the total amount of the 2-mercaptobenzoxazole of the formula II which is used, for example 8 to 30% by weight, preferably 10 to 25% by weight, of 2-chlorobenzoxazole of the formula I are initially introduced. It is normally not necessary to introduce initially a larger amount of 2-chlorobenzoxazole of the formula I. The 2-chlorobenzoxazole of the formula I is advantageously initially introduced in the form of a crude reaction mixture of a previous batch. Neither is it harmful if the reaction vessel still contains distillation residues of one or more preceding batches.

The 2-mercaptobenzoxazole of the formula II is advantageously added over a period of 0.5 to 5 hours, preferably 1 to 3 hours, either in portions or continuously. The rates at which chlorine is passed in and 2-mercaptobenzoxazole of the formula II is added are matched to each other in such a way that the reaction mixture always remains stirrable. If a melt of pure 2-chlorobenzoxazole of the formula I has initially been introduced the reaction is started at temperatures above the melting point of the final product of the formula I, for example at temperatures up to 100° C. The reaction temperature can be reduced to 0° C. in the course of the reaction.

In many cases the reaction is carried out within a temperature range of 60° to 10° C. The reaction is preferably carried out within a temperature range of 40° to 20° C., in particular if the 2-chlorobenzoxazole of the formula I is initially introduced in the form of a crude reaction mixture and/or if there is a danger of ring chlorinations. However, in any case it is necessary to select a temperature which is sufficiently high that the reaction mixture is still stirrable. After the total amount of 2-mercaptobenzoxazole of the formula II has been added, chlorine is passed into the reaction mixture at least until the amount of chlorine calculated from the reaction equation $II + Cl_2 \rightarrow I + HCl + S$ has been consumed. A better yield is obtained if chlorine is passed in until the amount calculated from the reaction equation $2\ II + 3Cl_2 \rightarrow 2\ I + 2HCl + S_2Cl_2$ has been consumed. It can be advantageous immediately to stop passing in chlorine when the amount thus calculated has been reached, in order to avoid undersirable ring chlorinations. However, in general it does no harm to pass in still more chlorine. The extreme case is then that $SCl_2$ is formed in place of $S_2Cl_2$, or rather mixtures of $SCl_2$ and $S_2Cl_2$, as in the reaction equation $II + 2Cl_2 \rightarrow I + HCl + SCl_2$. For this reason 1.5 mols of chlorine are preferably used per mol of 2-mercaptobenzoxazole of the formula II. The reaction mixture is worked up in a customary manner by distillation under reduced pressure.

The process according to the invention produces 2-chlorobenzoxazoles of the formula I in excellent yields and high purities, and the simultaneously formed sulphur chlorides $S_2Cl_2$ and/or $SCl_2$ are obtained in high purity without being contaminated by organic solvents. The spacetime yield of the reaction is very high, and the energy required is low since no solvent needs to be distilled. The reaction vessel need not be cleaned after every batch, since the distillation residue can remain in the reaction vessel for several batches without reducing yield and/or product quality. The 2-mercaptobenzoxazoles of the formula II which are required as starting compounds can be prepared in a manner which is in itself known from the corresponding ortho-aminophenols by reaction with sodium ethylxanthate or with carbon disulphide in the presence of a base.

EXAMPLE 1

150 g of pure 2,6-dichlorobenzoxazole (melting point: 49°–50° C.) are initially introduced in a 1 liter 4-necked flask equipped with a stirrer, internal thermometer, gas inlet tube and 30 cm column with Raschig rings, and melted in a water bath at 60° C. 835 g of 2-mercapto-6-chlorobenzoxazole are added to the melt little by little in the course of about 1 to 3 hours. Chlorine is passed in at the same time through the gas inlet tube. The rate at which 2-mercapto-6-chlorobenzoxazole is added and the chlorine stream are matched to each other in such a way that the contents of the flask always remain stirrable. By means of external cooling the internal temperature is kept initially below 60° C. and later reduced to room temperature. After all 2-mercapto-6-chlorobenzoxazole has been added, further chlorine is passed in until 480 g have been absorbed. Chlorine is passed in for a total of about 3 hours. The reaction mixture is distilled under a water-jet vacuum, with $S_2Cl_2$ passing over first at about 30° C., followed at 118° C. and under 24 mbar by about 920 g of 2,6-dichlorobenzoxazole.

Purity by gas chromatography: 99.8%, melting point: 49 to 50° C., and yield: 91% of theory.

Analysis of the $S_2Cl_2$ obtained: 47.2% of S and 52.9% of Cl (theoretically: 47.5% of S and 52.5% of Cl).

EXAMPLE 2

Example 1 is repeated, except that the material initially introduced is not pure 2,6-dichlorobenzoxazole but a crude undistilled reaction mixture as obtained in Example 1 and containing a corresponding amount of 2,6-dichlorobenzoxazole and a temperature of 30°–40° C. is maintained throughout the entire reaction. About 940 g of 2,6-dichlorobenzoxazole of the same purity are obtained.

Yield: 93% of theory.

EXAMPLE 3

The procedure as in Examples 1 and 2 is followed, except that 600 g of chlorine are passed in instead of 480 g. 2,6-dichlorobenzoxazole is obtained in the same yield and purity. However, the additional product obtained in this case is not pure $S_2Cl_2$ but a mixture of $SCl_2$ and $S_2Cl_2$.

EXAMPLE 4

The procedure as in Examples 1 to 3 is followed, except that a flask is used which still contains the distillation residues of preceding experiments. 2,6-Dichlorobenzoxazole is obtained in the same yield and purity.

EXAMPLE 5

Example 1 is repeated, except that 2-chlorobenzoxazole is initially introduced, a temperature range of 20°–40° C. is used from the start, 830 g of 2-mercaptobenzoxazole are added and 586 g of chlorine are passed in. About 910 g of 2-chlorobenzoxazole are obtained after distillation under a water-jet vacuum at 107° C. Traces of ring-chlorinated product can be detected in the distillation residue. Yield: 90% of theory.

EXAMPLE 6

Example 5 is repeated, except that 5-methyl-2-chlorobenzoxazole is initially introduced, 825 g of 5-methyl-2-mercaptobenzoxazole are added and 533 g of chlorine are passed in. About 830 g of 5-methyl-2-chlorobenzoxazole are obtained after distillation under a water-jet vacuum at 110° C.; yield: 81% of theory. Particular care must be taken in this case that a temperature of 40° C. is not exceeded at any time throughout the entire reaction, since in this case there is an increased danger of ring chlorination.

What is claimed is:

1. In the process for preparing 2-chlorobenzoxazoles of the formula

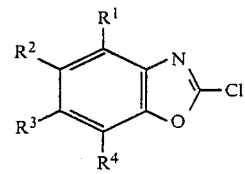

wherein each of $R^1$, $R^2$, $R^3$ and $R^4$ is independently of one another. H, chloro or alkyl having 1 to 4 carbon atoms, which comprises reacting chlorine with 2-mercaptobenzoxazoles of the formula

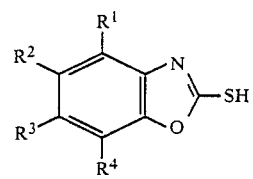

wherein the improvement comprises providing a melt of previously prepared 2-chloro-benzoxazole, adding the 2-mercaptobenzoxazole reactant to the 2-chlorobenzoxazole melt and simultaneously or subsequently passing chlorine into the melt, with the proviso that substituents $R^1$ to $R^4$ are identical in both the 2-chlorobenzoxazole melt and the 2-mercaptobenzoxazole reactant.

2. The process according to claim 1 wherein the 2-chlorobenzoxazole melt is a crude reaction mixture of a previous batch.

3. The process according to claim 1 wherein the 2-mercaptobenzoxazole reactant is added to the melt in portions.

4. The process according to claim 1 wherein the 2-mercaptobenzoxazole reactant is added to the melt continuously.

5. The process according to claim 1 wherein chlorine is passed into the melt at such a rate that the reaction mixture remains stirrable.

6. The process according to claim 1 wherein about 1 to 2 moles of chlorine are passed into the melt for each mole of 2-mercaptobenzoxazole reactant.

7. The process according to claim 6 wherein about 1.5 moles of chlorine are passed into the melt for each mole of 2-mercaptobenzoxazole reactant.

8. The process according to claim 1 wherein the reaction is carried out at temperatures of 0° C. to 100° C.

9. The process according to claim 8 wherein the reaction is carried out at temperatures of 20° C. to 40° C.

10. The process according to claim 1 wherein one of $R^1$, $R^2$, $R^3$ or $R^4$ is chloro the other three are H.

11. The process according to claim 1 wherein each of $R^1$ to $R^4$ is H.

* * * * *